(12) United States Patent
Hamill et al.

(10) Patent No.: US 12,013,450 B2
(45) Date of Patent: Jun. 18, 2024

(54) PET TRANSMISSION SOURCE BASED ON CONTINUOUS BED MOTION

(71) Applicant: Siemens Medical Solutions USA, Inc., Malvern, PA (US)

(72) Inventors: James Hamill, Knoxville, TN (US); Mohammadreza Teimoorisichani, Knoxville, TN (US); Charles Russell Buchanan, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 251 days.

(21) Appl. No.: 17/724,667

(22) Filed: Apr. 20, 2022

(65) Prior Publication Data
US 2023/0341489 A1 Oct. 26, 2023

(51) Int. Cl.
*G01R 33/48* (2006.01)
*A61B 6/00* (2024.01)
(Continued)

(52) U.S. Cl.
CPC ............ *G01R 33/481* (2013.01); *A61B 6/037* (2013.01); *A61B 6/0407* (2013.01);
(Continued)

(58) Field of Classification Search
CPC .. G01R 33/481; G01R 33/4812; A61B 6/037; A61B 6/0407; A61B 6/4417;
(Continued)

(56) References Cited

U.S. PATENT DOCUMENTS

| 5,750,991 A | * | 5/1998 | Moyers | .................. | A61B 6/037 |
| | | | | | 250/363.04 |
| 6,388,244 B1 | * | 5/2002 | Gagnon | ............... | A61B 6/4258 |
| | | | | | 250/363.04 |

(Continued)

FOREIGN PATENT DOCUMENTS

WO   2021222921 A1   11/2021

OTHER PUBLICATIONS

Mollet, Pieter, et al. "Improvement of attenuation correction in time-of-flight PET/MR imaging with a positron-emitting source." Journal of Nuclear Medicine 55.2 (2014): 329-336. (Year: 2014).*

(Continued)

*Primary Examiner* — Sean D Mattson (57) ABSTRACT

A method for generating transmission information in a time-of-flight positron emission tomography (PET) scanner having a patient tunnel and a plurality of PET detector rings. The PET scanner uses continuous bed motion to move a patient bed and patient through the patient tunnel. The patient receives a positron-emitting radioisotope dose prior to undergoing a PET scan. The method includes storing a positron-emitting radioisotope in a radiation shielded container. The method also includes moving the radioisotope into a stationary vessel located adjacent to the PET detectors and within a field of view of the PET scanner at substantially the same time that the patient receives the radioisotope dose to form a stationary transmission source wherein transmission information is generated while the bed undergoes continuous bed motion. Further, the method includes withdrawing the radioisotope from the vessel when the PET scan is complete and storing the radioisotope in the container.

17 Claims, 7 Drawing Sheets

(51) Int. Cl.
*A61B 6/03* (2006.01)
*A61B 6/04* (2006.01)
*G01T 1/29* (2006.01)
*G06T 11/00* (2006.01)

(52) U.S. Cl.
CPC ........ *A61B 6/4417* (2013.01); *G01R 33/4812* (2013.01); *G01T 1/2985* (2013.01); *G06T 11/003* (2013.01); *A61B 6/481* (2013.01); *A61B 6/5235* (2013.01); *G06T 2207/10088* (2013.01); *G06T 2207/10104* (2013.01)

(58) Field of Classification Search
CPC ..... A61B 6/481; A61B 6/5235; G01T 1/2985; G06T 11/003; G06T 2207/10104; G06T 2207/10088
See application file for complete search history.

(56) References Cited

U.S. PATENT DOCUMENTS

| | | | |
|---|---|---|---|
| 6,449,331 | B1 | 9/2002 | Nutt et al. |
| 6,963,065 | B2 | 11/2005 | Conti et al. |
| 7,848,559 | B2 | 12/2010 | Defrise et al. |
| 7,876,941 | B2 | 1/2011 | Panin et al. |
| 2007/0135702 | A1* | 6/2007 | Matsuzaki .............. A61B 6/037 600/407 |
| 2008/0296505 | A1* | 12/2008 | Cooke .................... A61B 6/037 250/363.04 |
| 2010/0074498 | A1* | 3/2010 | Breeding .............. G06T 11/005 382/131 |
| 2014/0056500 | A1 | 2/2014 | Bal et al. |
| 2014/0217294 | A1 | 8/2014 | Rothfuss et al. |
| 2015/0065869 | A1* | 3/2015 | Daghighian ......... A61B 6/5258 600/425 |
| 2015/0241576 | A1 | 8/2015 | Rothfuss et al. |

OTHER PUBLICATIONS

Mollet, Pieter, et al. "Simultaneous MR-compatible emission and transmission imaging for PET using time-of-flight information." IEEE transactions on medical imaging 31.9 (2012): 1734-1742. (Year: 2012).*

Ramsey D. Badawi, "Aspects of Optimisation and Quantification in Three-Dimensional Positron Emission Tomography", Mar. 1998, pp. 1-19 and pp. 20-57, PHD Thesis submitted to the University of London, The Clinical PET Centre, Guy's and St. Thomas' Hospital, UMDS, London.

M. Xu, P.D. Cutler, and W.K. Luk, "Adaptive, Segmented Attenuation Correction for Whole-Body PET Imaging", IEEE Transactions on Nuclear Science, Feb. 1996, pp. 331-336, vol. 43, No. 1, IEEE, US.

Habib Zaidi and Bruce Hasegawa, "Determination of the Attenuation Map in Emission Tomography", The Journal of Nuclear Medicine, Feb. 2003, pp. 301-302, vol. 44, No. 2, Society of Nuclear Medicine and Molecular Imaging, US.

C.C. Watson, W.F. Jones, T. Brun, K. Baker, K. Vaigneur and J. Young, "Design and Performance of a Single Photon Transmission Measurement for the ECAT ART", 1997 IEEE Nuclear Science Symposium Conference Record, 1997, pp. 1366-1370, vol. 2, IEEE, US.

Edward J. Hoffman, Thomas M. Guerrero, Guido Germano, Ward M. Digby and Magnus Dahlbom, "PET System Calibrations and Corrections for Quantitative and Spatially Accurate Images", IEEE Transactions on Nuclear Science, Feb. 1989, pp. 1108, vol. 36, No. 1, IEEE, US.

Dale L. Bailey, David W. Townsend, Peter E. Valk and Michael N. Maisey, "Positron Emission Tomography Basic Sciences", 2005, pp. 116-119, Springer Science & Business Media, London.

Johan Nuyts, Patrick Dupont, Sigrid Stroobants, Roel Benninck, Luc Mortelmans and Paul Suetens, "Simultaneous Maximum a Posteriori Reconstruction of Attenuation and Activity Distributions from Emission Sinograms", IEEE Transactions on Medical Imaging, May 1999, pp. 393-403, vol. 18, No. 5, IEEE, Belgium.

Lars-Eric Adam, Joachim Zaers, Hermann Ostertag, Herbert Trojan, Matthias E. Bellemann and Gunnar Brix, "Performance Evaluation of the Whole-Body PET Scanner ECAT EXACT HR+ Following the IEC Standard", IEEE Transactions on Nuclear Science, Jun. 1997, pp. 1172-1179, vol. 44, No. 3, IEEE, US.

Maurizio Conti, "Focus on time-of-flight PET: the benefits of improved time resolution", European Journal of Nuclear Medicine and Molecular Imaging, Jan. 13, 2011, pp. 1147-1157, vol. 38, Springer-Verlag, Switzerland.

Nicole T. Ranger, Christopher J. Thompson and Alan C. Evans, "The Application of a Masked Orbiting Transmission Source for Attenuation Correction in PET", The Journal of Nuclear Medicine, Jun. 1989, pp. 1056-1068, vol. 30, No. 6, Society of Nuclear Medicine and Molecular Imaging, US.

U.S. Appl. No. 61/894,013, filed Oct. 22, 2013, entitled "Time of Flight PET Transmission Measurements Based on Backscatter".

* cited by examiner

PET TRANSMISSION SOURCE BASED ON CONTINUOUS BED MOTION

TECHNICAL FIELD

Aspects of the present invention relate to a transmission source for a positron emission tomography (PET) scanner, and more particularly, to a transmission source that includes a stationary tube for receiving a radiotracer at substantially the same time a patient receives a radiotracer dose wherein the radiotracer is removed from the tube when the PET scan is complete and wherein a patient bed of the PET scanner undergoes continuous bed motion during the PET scan.

BACKGROUND

Positron emission tomography (PET) is a nuclear medicine imaging technique that produces a three-dimensional image representing the distribution of positron emitting isotopes within a patient's body. In this technique, a radiotracer such as fluorodeoxyglucose (FDG) is injected into the patient. As the radioisotope in the radiotracer undergoes positron emission decay (also known as positive beta decay), it emits the antimatter counterpart of electrons. As the positrons lose energy, they ultimately encounter and annihilate with electrons, usually producing a pair of annihilation (gamma) photons moving in opposite directions. The PET system determines the line along which the annihilation occurred, by detecting the pair of gamma photons in time coincidence.

Attenuation in PET imaging is the loss of detection of true coincidence events because of their absorption in the body or due to their scattering out of the PET detector field of view (FOV). This causes undesirable image artifacts and image distortion in PET images. Attenuation correction is frequently used to perform image reconstruction of PET images. An integrated positron emission tomography and x-ray computed tomography (PET/CT) imaging system may be used to generate data that is used for attenuation correction. In this arrangement, CT data obtained during a CT scan performed by the CT portion of the PET/CT imaging system is used to generate an attenuation map of density differences throughout a patient's body. The attenuation map is then used to correct for the absorption of the photons emitted from fluorodeoxyglucose decay in the emission scan.

PET scanner designs have been proposed wherein a CT scanner is not used to generate CT data for attenuation correction. In one PET scanner design, attenuation correction is derived from background radiation emitted in the lutetium-based scintillation crystals in the detectors themselves (e.g. LSO or LYSO scintillation crystals, for example). However, the intensity of the LSO background radiation is generally too low to be used in patient scans of normal duration.

Alternatively, attenuation correction may be derived from a transmission scan that uses a positron-emitting transmission source. In early generation PET scanners, attenuation correction was derived from either a solid or liquid positron-emitting transmission source that was stationary. Subsequent PET scanners may use a moveable transmission source in order to provide a more practical and compact configuration. In one configuration, the transmission source is in the form of a rod that rotates or orbits relative to a ring of PET detectors. However, this configuration reduces the FOV and requires onboard storage of a radioactive source in the PET scanner, thus necessitating shielding to protect the patient from radiation as well as other personnel who must work in proximity to the PET scanner. Further, a motor for rotating the transmission source is required along with septa to reduce PET detector dead time and scatter. In another configuration, point transmission sources are used in a rotating PET scanner wherein the point sources are moved to a variety of different axial positions in a raster scan pattern to create a series of circles around the patient. Further, attenuation correction may be derived from a transmission scan that uses a narrow tube that includes radioactive material. However, this arrangement also requires radiation shielding to protect the patient from radiation.

The combination of PET imaging and CT imaging in an integrated PET/CT medical imaging system provides more precise alignment or correlation of the functional imaging obtained by PET with anatomic imaging obtained by CT scanning. However, such integrated PET/CT imaging systems require the additional CT scanning hardware to be integrated with the PET imaging hardware. Thus, it would be desirable if a transmission type scan data can be obtained using a PET scanner without the additional transmission scanning hardware such as a CT scanner.

SUMMARY OF THE INVENTION

A method for generating transmission information in a time-of-flight positron emission tomography (PET) scanner having a patient tunnel and a plurality of PET detector rings. The PET scanner uses continuous bed motion to move a patient bed having a patient through the patient tunnel wherein the patient receives a positron-emitting radioisotope dose prior to undergoing a PET scan. The method includes storing a positron-emitting radioisotope in a radiation shielded container. The method also includes moving the radioisotope into a stationary vessel located adjacent to the PET detector rings and within a field of view of the PET scanner at substantially the same time that the patient receives the radioisotope dose to form a stationary transmission source wherein transmission information is generated while the patient bed undergoes continuous bed motion. Further, the method includes withdrawing the radioisotope from the vessel when the PET scan is complete and storing the radioisotope in the container.

A transmission source is also disclosed for a positron emission tomography (PET) scanner having a plurality of PET detector rings and a patient tunnel defined by a scanner cover. The PET scanner uses continuous bed motion to move a patient bed having a patient through the patient tunnel wherein the patient receives a positron-emitting radioisotope dose prior to undergoing a PET scan. The transmission source includes a stationary tube element having a receiving end, wherein the tube is attached to a scanner surface of the scanner cover located adjacent to the PET detector rings and within a field of view of the PET scanner. The transmission source also includes a pump device fluidly connected to the receiving end, wherein the pump device introduces a positron-emitting radioisotope into the tube at substantially the same time that the patient receives the radioisotope dose wherein transmission information is generated while the patient bed undergoes continuous bed motion. Further, the radioisotope is withdrawn from the tube when the PET scan is complete.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

DETAILED DESCRIPTION

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

The invention may be used in conjunction with a standalone positron emission tomography (PET) imaging system, an integrated positron emission tomography and x-ray computed tomography (PET/CT) imaging system and an integrated magnetic resonance and positron emission tomography (MR/PET) imaging system although it is understood that the invention may be used in other imaging systems.

Figure 1:
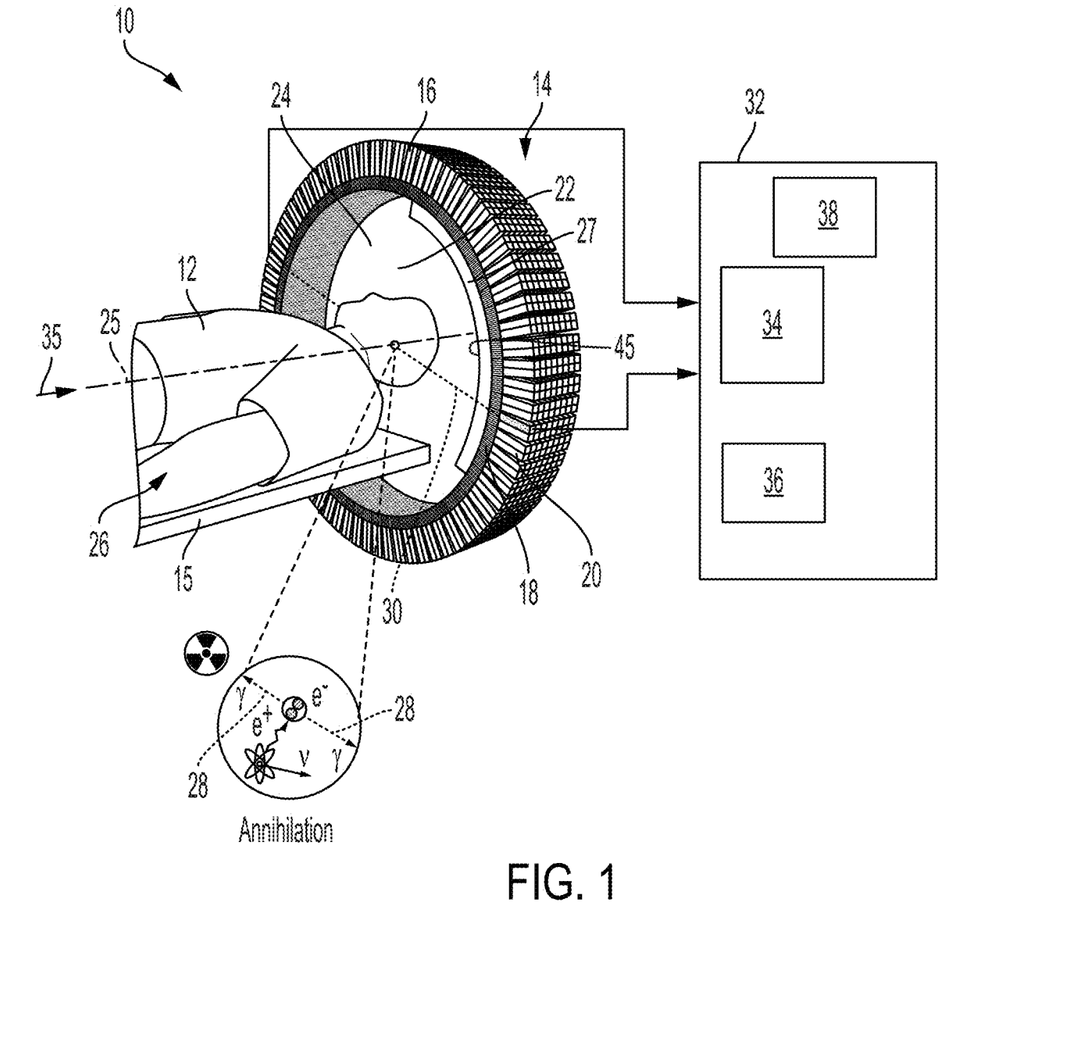
FIG. 1 is a schematic view of an example standalone positron emission tomography (PET) scanner system in which the inventive concepts disclosed herein can be implemented.

Referring to FIG. 1, a schematic view of an example standalone PET scanner system 10 is shown in which the inventive concepts disclosed herein can be implemented. A patient 12 or human subject for PET scanning is positioned horizontally on a continuously moveable patient bed 15 located on a horizontal axis 25 of the PET scanner 10. The PET scanner includes a PET gantry 14 having a plurality of PET detector rings 16. Each PET detector ring 16 includes a plurality of scintillating crystals 18 and an associated PET detector 20. An interior of each PET detector ring 16 encloses a space 22 that defines a field of view (FOV) of the PET scanner 10. The PET scanner 10 further includes an annular scanner cover 27 (shown as a partial view) located within the space 22 and adjacent to the PET detector rings 16. The scanner cover 27 defines a patient tunnel 24 of the PET gantry 14. Before a PET scan is performed, a positron-emitting radioisotope dose 26 is introduced into the patient 12 on metabolically active molecules. The metabolically active molecules are then carried to an organ of interest by the patient's blood flow.

The patient bed 15 is coupled to a motor drive apparatus and is designed to provide known continuous bed motion without stationary periods. In regard to continuous bed motion and rebinning techniques, the entire disclosure of U.S. Patent Publication No. 2010/0074498 A1, published on Mar. 25, 2010 and entitled ON-LINE TOF-PET MASHED REBINNING FOR CONTINUOUS BED MOTION ACQUISITIONS is hereby incorporated by reference in its entirety. During a PET scan, the patient bed 15 continuously moves the patient 12, without stationary periods, along the horizontal axis 25 of the PET scanner 10 and through the PET gantry 14 in a horizontal direction 35.

When a positron emitted from the radioisotope now inside the human subject encounters an electron, both are annihilated (i.e., annihilation events) yielding two gamma photons 28 that travel in approximately opposite directions. The annihilation events are identified by a time coincidence between the detection of the two gamma photons 28 by two oppositely disposed detectors by the interaction of the gamma photons with the detector's scintillating crystals 18, i.e., the gamma photon emissions are detected virtually simultaneously by each detector 20. When two oppositely traveling gamma photons strike corresponding oppositely disposed detectors to produce a time coincidence event, the photons identify a line of response (LOR) 30 along which the annihilation event has occurred.

Images of metabolic activity in the patient 12 (nuclear medical images) are reconstructed by computer analysis. The PET scanner system 10 includes a system controller 32 connected to and in communication with the PET detector rings 16. The PET scanner system 10 further comprises a data processing unit (event detection unit) 34 which determines and evaluates coincidence events generated by the pair of gamma photons 28 and forwards this information to an image processing unit (computational unit) 36. Detector pairs associated to each LOR 30 produce many coincidence events during a measurement session (i.e., data acquisition scan). The PET scanner system 10 further includes at least one machine-readable storage medium 38 that is encoded with a computer program code which when executed by the system controller 32, the system controller 32 performs various operational functions of the PET scanner system 10.

Many PET scanners use known time-of-flight (TOF) techniques that provide improved image quality. When two back-to-back photons are emitted by the annihilation of a positron, the photons reach two opposite detectors of a PET scanner at different times. The TOF difference is proportional to the path length difference of the two photons, and this provides information on the position of the annihilation along the LOR 30 to ultimately provide an improved signal-to-noise ratio (SNR) and image quality. In regard to PET imaging, the entire disclosures of U.S. Pat. No. 7,848,559 B2, issued on Dec. 7, 2010 to Defrise et al. and entitled DISCRETE AXIAL RE-BINNING OF TIME-OF-FLIGHT POSITRON EMISSION TOMOGRAPHY DATA and that of U.S. Pat. No. 7,876,941 B2, issued on Jan. 25, 2011 to Panin et al. and entitled INCORPORATION OF AXIAL SYSTEM RESPONSE IN ITERATIVE RECONSTRUC- TION FROM AXIALLY COMPRESSED DATA OF CYLINDRICAL SCANNER USING ON-THE-FLY COMPUTING are incorporated herein by reference in their entirety.

Attenuation in PET imaging is the loss of detection of true coincidence events because of their absorption in the body or due to their scattering out of the detector FOV. This causes undesirable image artifacts and image distortion in PET images. Attenuation correction for performing image reconstruction of PET images may be derived from a transmission scan that uses a positron-emitting transmission source. In addition, image data may be reconstructed through the use of a known iterative reconstruction algorithm such as the maximum likelihood transmission reconstruction (MLTR) algorithm. In regard to reconstruction techniques, the entire disclosure of a paper by Nuyts et al., entitled "Simultaneous Maximum A Posteriori Reconstruction of Attenuation and Activity Distributions from Emission Sinograms" published in IEEE Transactions on Medical Imaging, Vol. 18, no. 5 (May 1999), pp. 393-403 is hereby incorporated by reference in its entirety.

Figure 2:
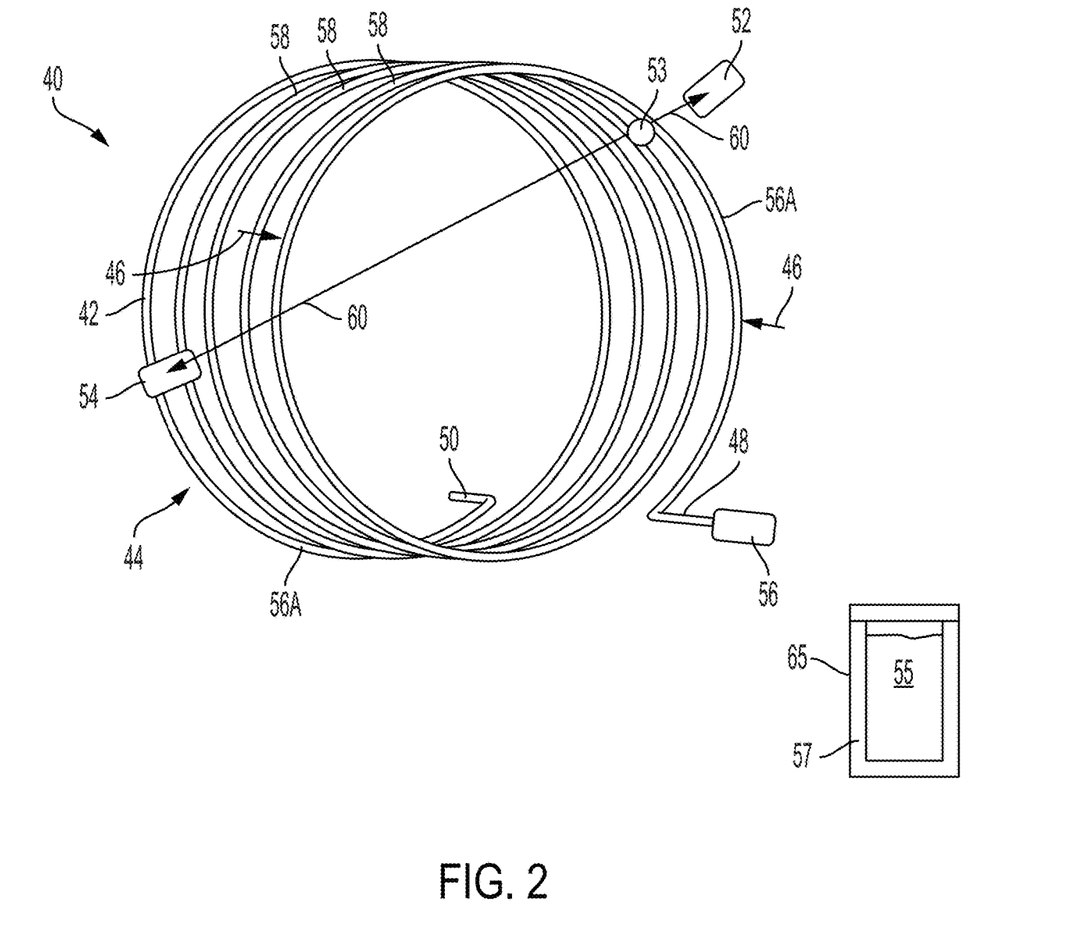
FIG. 2 shows an embodiment of a stationary PET transmission source in accordance with an aspect of the invention.

Referring to FIG. 2, an embodiment of a stationary PET transmission source 40 in accordance with an aspect of the invention is shown. The transmission source 40 includes a hollow tube element 42 configured as a coil or spiral shape 44 having an outer diameter 46. The transmission source 40 further includes a receiving end 48 for receiving a liquid radiotracer 55 including an 18F radioisotope such as $^{18}$F-fluorodeoxyglucose (FDG) and a closed end 50. The tube 42 is attached to a scanner surface 45 of the scanner cover 27 (see FIGS. 1 and 3) such that the tube 42 is stationary. Further, the tube 42 is located on the scanner cover 27 in front of, or adjacent to, the PET detectors 20 of the PET scanner 10 (see FIG. 1) and thus is within the FOV. In FIG. 2, the outer diameter 46 of the spiral shape 44 is shown located in between exemplary first 52 and second 54 PET detectors. A pump device 56 for introducing the radiotracer 55 into the tube 42 is fluidly connected to the receiving end 48. In an embodiment, the pump device 56 may be a syringe that injects the radiotracer 55 into the tube 42. The tube 42 may be fabricated from a thermoplastic such as polyether ether ketone and may have an inner diameter of approximately 0.8 mm. The transmission source includes a plurality of spiral tube sections 58. In an embodiment, the transmission source may have approximately five spiral tube sections 58 arranged to cover an axial range along horizontal axis 25 that includes the PET detector rings 16, although it is understood that additional or fewer spiral tube sections may be used. The transmission source 40 further includes an additional half-spiral tube section 56A that includes the receiving 48 and closed 50 ends. In an embodiment, the spiral tube sections 58 may be separated by a pitch of approximately 6 cm and have a diameter of approximately 78 cm and contain a volume of approximately 7 ml of radioactive liquid. For example, a 1 mCi dose of a radiopharmaceutical may be used which only requires a relatively small amount of radiation shielding to protect the patient 12 and other personnel that operate the PET scanner 10 from radiation emitted by the pharmaceutical. In an alternate embodiment, a plurality of separate ring shaped tube sections may be used instead of a single spiral shaped tube. In this embodiment, each ring shaped tube section includes an associated pump device for introducing the radiotracer 55 into a respective tube section. In yet another embodiment, a single pump device may be used and the ring shaped tube sections may be connected to each other by a crossover section to enable the radiotracer 55 to flow between the ring shaped tube sections.

The liquid radiotracer 55 is stored in a container element 65 that includes radiation shielding 57 to protect the patient and other personnel that operate the PET scanner 10 from radiation emitted by the radiotracer 55. In operation, a relatively small amount of a liquid radiotracer 55 from the container element 65 is introduced into the transmission source 40 by the pump 56 via the receiving end 48 at substantially the same time that a radiotracer dose is administered to the patient 12 prior to PET scanning. By way of illustration, FIG. 1 depicts an exemplary decay 53 from the radiotracer 55 in the transmission source 40 which results in the generation of two 511 keV photons 60 that are detected by the first 52 and second 54 PET detectors. The patient bed 15 then undergoes continuous bed motion as previously described and is moved relative to the stationary transmission source 40 and the PET scanner 10 during scanning. Due to the continuous bed motion, radioactivity emitted from the transmission source 40 is detected by the first 52 and second 54 PET detectors at different relative positions as the patient bed 15 moves. This effectively creates a cylindrical sheet source around the patient 12 since the rebinner (i.e., hardware and/or software associated with a known rebinning operation) assumes that the PET detectors 20 in the PET detector rings 16 move across the patient although the PET detectors 20 are stationary. Transmission information is then acquired during the PET scan. Upon completion of the PET scan, the liquid radiotracer 55 is withdrawn from the transmission source 40 by the pump device 56 and stored in the container element 65 to minimize patient exposure to radiation.

A blank or reference scan may be performed before any patient transmission scans. The blank scan is a measurement by the PET scanner 10 without the patient 12, that is, with nothing but air between the transmission source 40 and the PET detectors 20. A transmission scan is then performed with the patient 12 in the PET scanner FOV as previously described. A ratio is then calculated between coincidence counts detected during the blank scan relative to coincidence counts detected during the transmission scan that is then used as a correction factor for each transmission LOR.

In transmission PET, it is desirable to have a balance between high activity and low PET detector dead time since the transmission sources are close to the PET detectors 20. In accordance with an aspect of the invention, a suitable balance is achieved by using multiple turns of the spiral tube 42. In another aspect, hardware and/or software of the PET scanner 10 is configured so that the coincidence windows defined by the FOV of the PET scanner 10 are sufficiently wide to enable detection of radiation from the transmission source 40. In addition, conventional or normal PET energy windows typically used by the PET scanner 10 to check the energy of each photon during data acquisition are maintained. Further, data acquisition may also be performed by using a singles mode with respect to coincidences.

Figure 3:
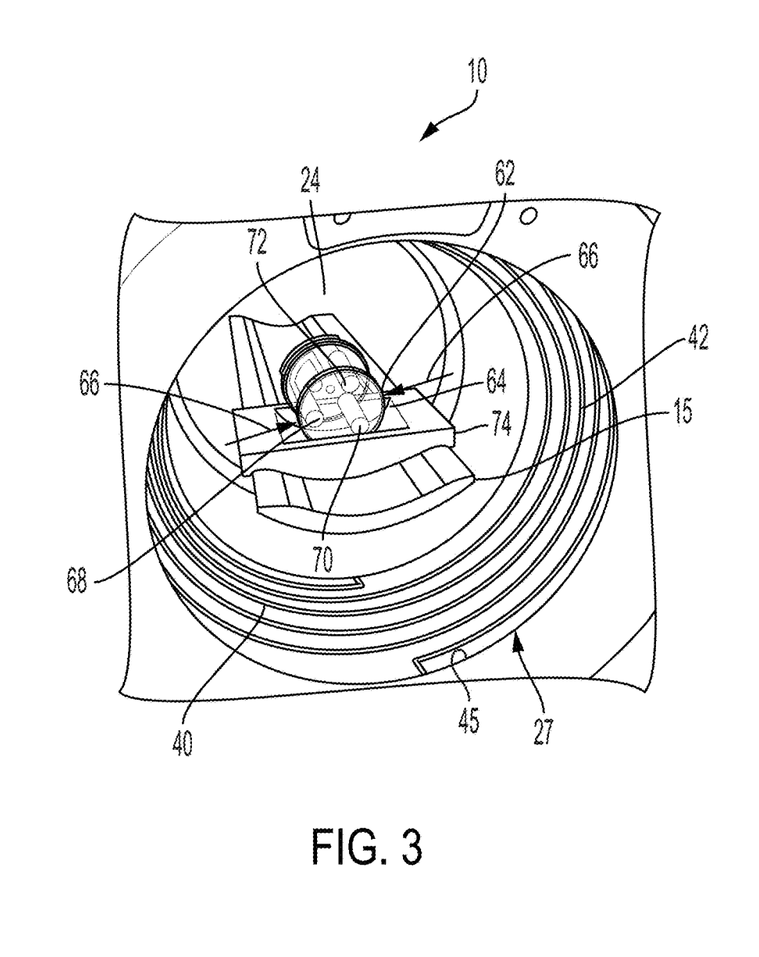
FIG. 3 is a perspective view of a prototype phantom for testing the transmission source.

Referring to FIG. 3, a perspective view of a prototype phantom 62 for testing the transmission source 40 is shown. In accordance with an aspect of the invention, the tube 42 of the transmission source 40 is attached to the scanner surface 45 in a portion of the scanner cover 27 that is in front of, or adjacent to, the PET detectors 20 of the PET scanner 10 (see FIG. 1) and thus is stationary. The phantom 62 includes a body 64 having a cylindrical shape defined by a body diameter 66. The body 64 includes first 68, second 70 and third 72 portions wherein the body 64 has a first density, the first 68 and second 70 portions are air filled and are less dense than the body 64 and the third portion 72 includes a material that is denser than the body 64. The phantom 62 is shown supported on the patient bed 15 of the PET scanner 10 by a support element 74 prior to being moved into the tunnel 24.

Figure 4:
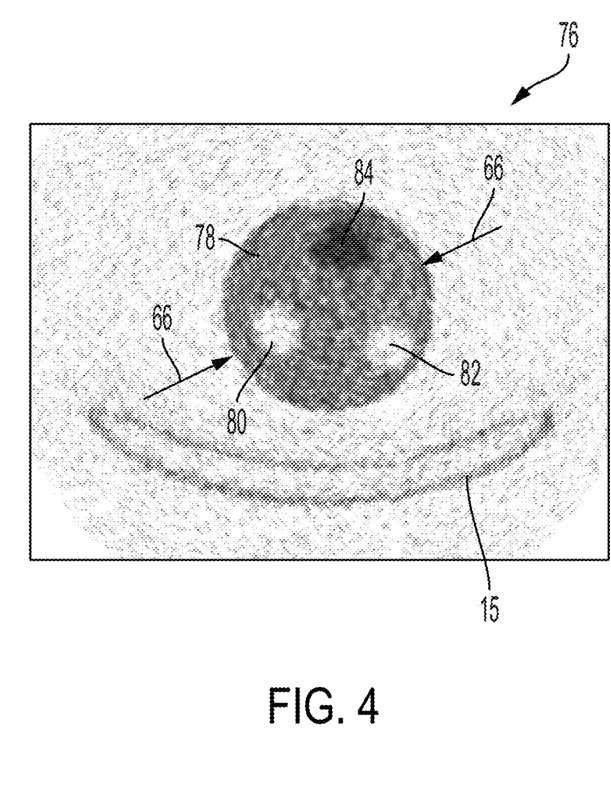
FIG. 4 shows a mu-map derived from scanning the phantom.

In accordance with an aspect of the invention, the patient bed 15 and phantom 62 are moved through the tunnel 24 using continuous bed motion as previously described. Referring to FIG. 4, a mu-map 76 (i.e., a spatial map of photon attenuation coefficients) derived from scanning the phantom 62 is shown. The mu-map 76 depicts a first gray area 78 defined by the body diameter 66 and first 80 and second 82 gray areas that are lighter than the first gray area 78 thus indicating areas that are less dense than the first gray area 78. In addition, the mu-map 76 depicts a third gray 84 area that is darker than the first gray area 78 thus indicating an area that is denser than the first gray area 78. Thus, the first gray area 78 corresponds to the body 64 and the first 80, second 82 and third 84 gray areas correspond to the first 68, second 70 and third 72 portions, respectively, of the body 64. Thus, the densities depicted in mu-map 76 correspond to the actual densities of the phantom 62.

In other embodiments, radioactivity is stored out of the PET scanner FOV in the shielded container element 65. The radioactivity may be stored in the container 65 (see FIG. 2) for an extended period of time that may span months or years. The radioactivity could comprise a radioactive compound dissolved in water, or a coiled irradiated wire, tube or set of radioactive beads. In an embodiment, a length of wire including 22Na or 64Cu may be used that is stored on a spool thus rendering the wire compact and easily shielded. The wire can then be extended from the spool and formed into a spiral-shaped tube or conduit. In yet another embodiment, the transmission source may be fabricated from a cured solid such as Ge-68 in polyurethane. For reference, the use of copper wires enriched with positron-emitting copper-64 in PET was described by L. E. Adam et al., "Performance Evaluation of the Whole-Body PET Scanner ECAT EXACT HR+ Following the IEC Standard" in IEEE Transactions on Nuclear Science, Volume 44, no. 3, (June 1997), pp. 1172-1179.

Acquiring transmission information during a PET scan has several advantages. In particular, transmission information acquired during a PET scan is more accurate than a mu map derived from a CT scan, such as when using a PET/CT imaging system, since the transmission information is acquired simultaneously with the PET scan. Thus, the registration of the two modalities is automatic, with no assumption that the patient did not move between CT and PET scans. Further, by acquiring transmission information during a PET scan, the CT scanner may be eliminated altogether. This substantially reduces the size and cost of the imaging system and also eliminates well-known artifacts that may occur during CT scanning, thus improving accuracy. In addition, by acquiring transmission information during a PET scan, the size of the FOV equals the PET scanner FOV so that a patient's arms are not truncated as occurs when using the CT scanner. Further, in comparison with transmission imaging based on LSO background radiation, a much lower scanning time is needed. A still further advantage is that PET scanner coincidence electronics that use TOF based coincidence measurements provide a wider TOF range. Alternatively, when using a PET/CT imaging system, the transmission information acquired during a PET scan may be used to complement CT based attenuation maps. Moreover, a CT based attenuation map may be algorithmically compared to a PET based attenuation map and in the case of discrepancy the PET based map may be used to replace the CT based map in PET image reconstruction.

Figure 5A:
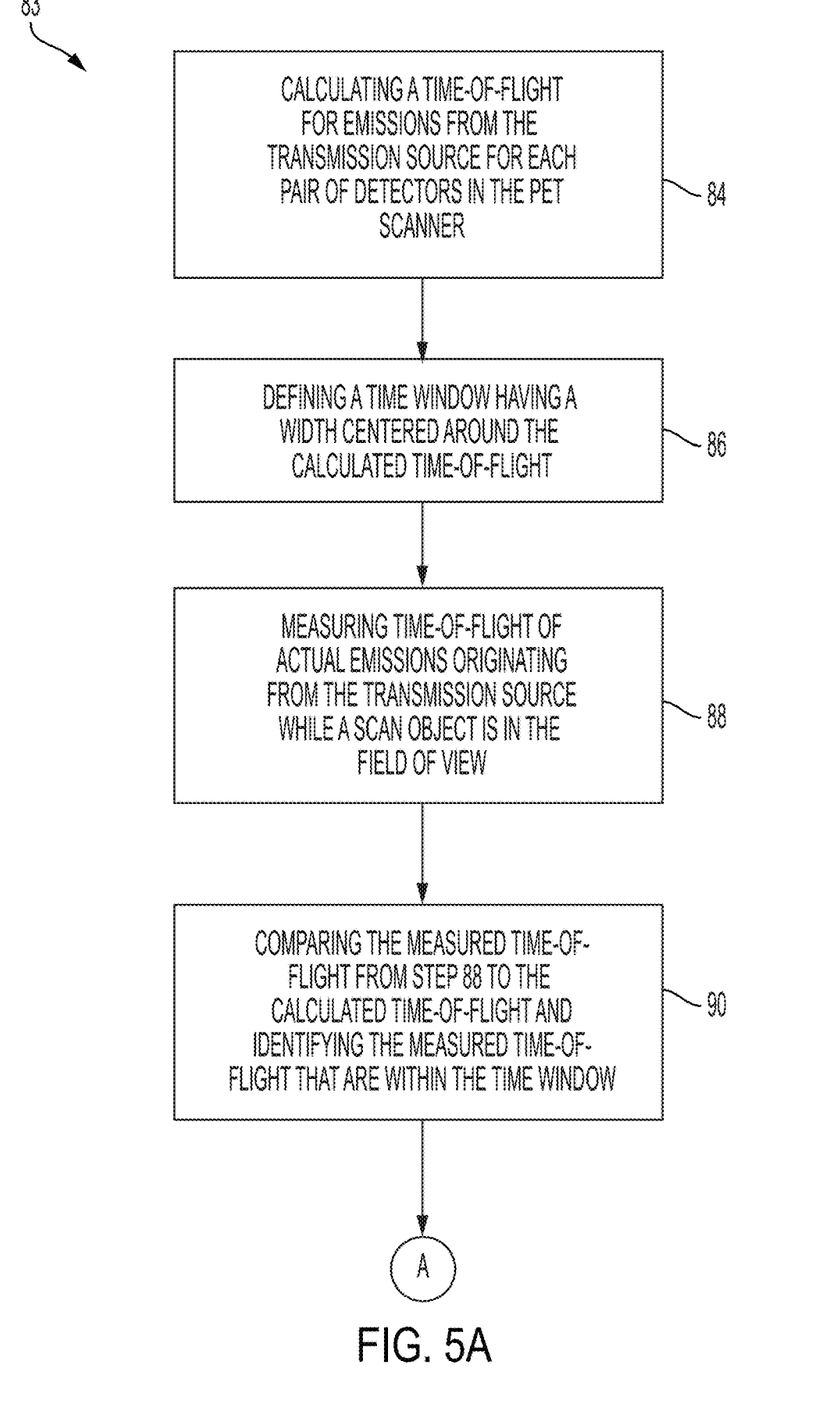
FIGS. 5A-5B illustrate a method for forming a PET attenuation map for a time-of-flight PET scanner in accordance with the invention.
Figure 5B:
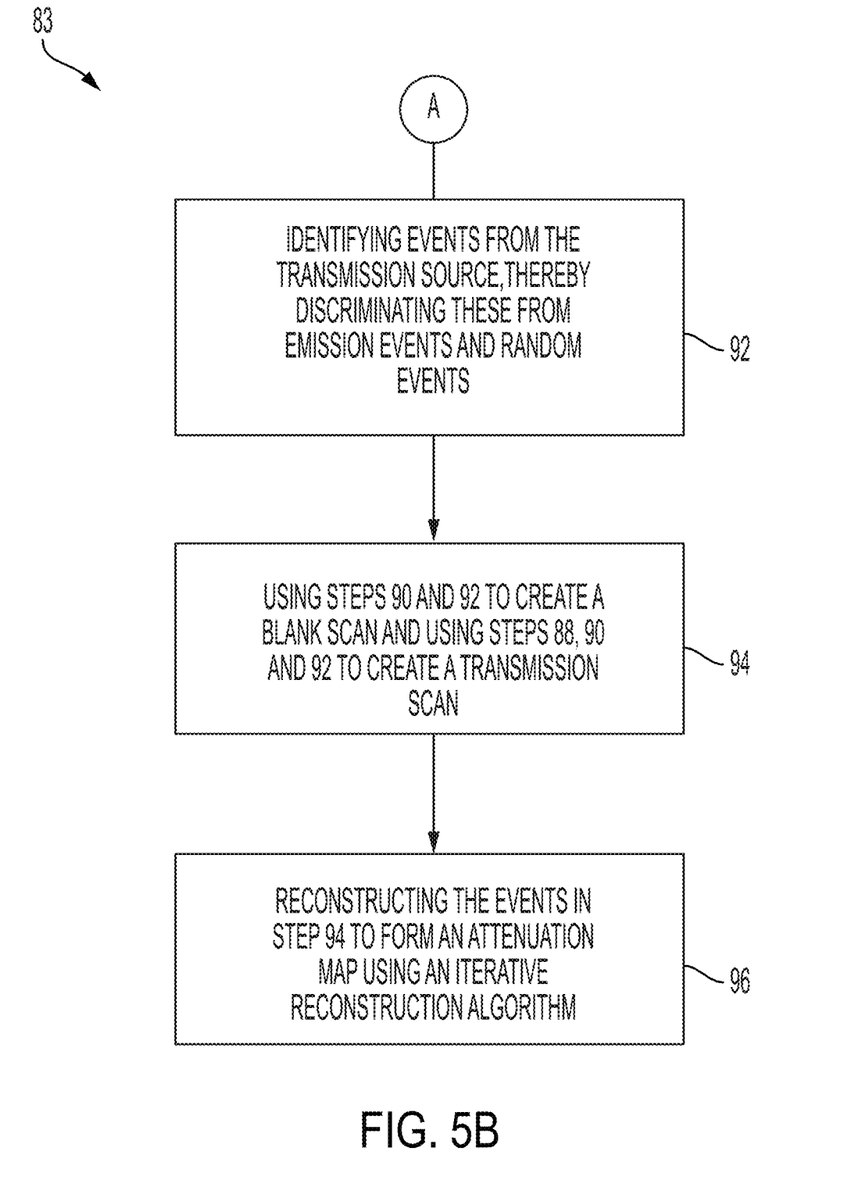

Referring to FIGS. 5A-5B, a method 83 for forming a PET attenuation map for a time-of-flight PET scanner in accordance with the invention is shown. In regard to generating attenuation maps, the entire disclosure of U.S. Patent Publication No. 2015/0241576 A1, published on Aug. 27, 2015 and entitled METHOD AND APPARATUS FOR COMPENSATING FOR SCATTERING OF EMISSION GAMMA PHOTONS FOR PET IMAGING is hereby incorporated by reference in its entirety.

The method 83 includes calculating a time-of-flight for emissions from the transmission source 40 for each pair of detectors in the PET scanner 10 at Step 84. At Step 86, a time window having a width centered around the calculated time-of-flight is defined. At Step 88, the time-of-flight of actual emissions originating from the transmission source 40 is measured while a scan object is in the field of view. At Step 90, the measured time-of-flight from Step 88 is compared to the calculated time-of-flight and the measured time-of-flight that are within the time window are identified. At Step 92, events from the transmission source 40 are identified, thereby discriminating these events from emission events and random events. At Step 94, Steps 90 and 92 are used to create a blank scan, and Steps 88, 90, and 92 are used to create a transmission scan. At Step 96, Step 94 is reconstructed to form an attenuation map using an iterative reconstruction algorithm.

Figure 6:
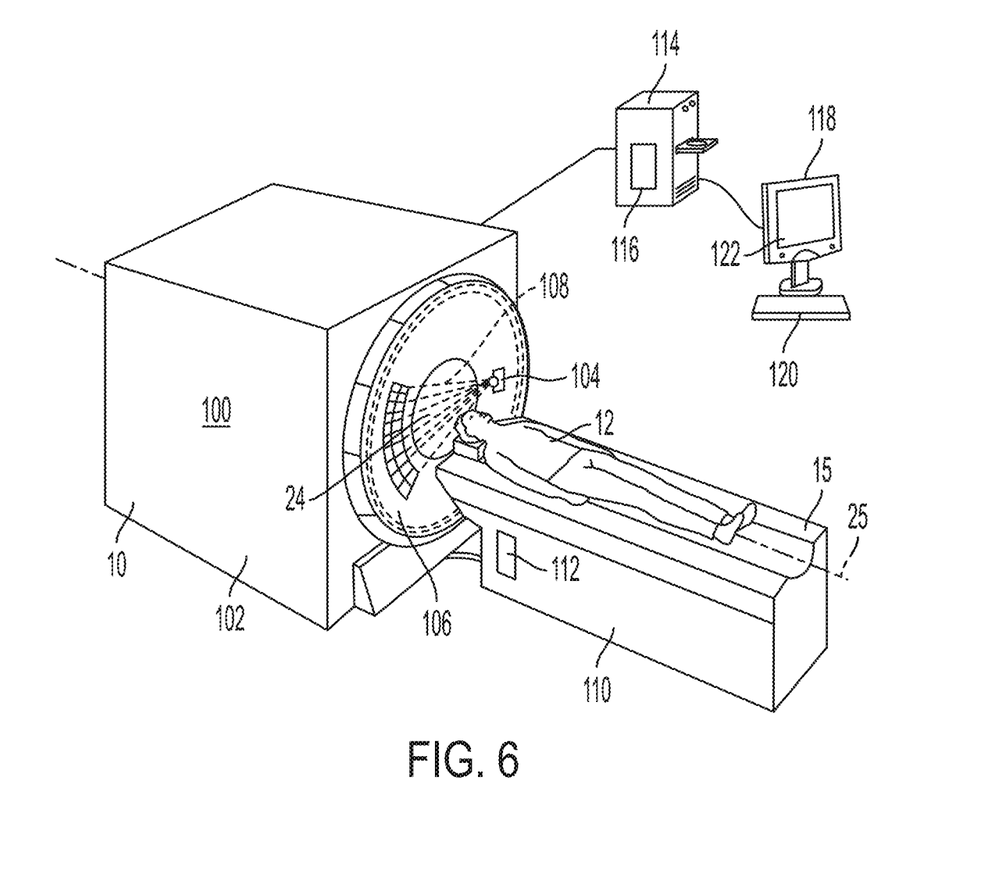
FIG. 6 depicts an integrated PET/x-ray computed tomography (CT) imaging system having the PET scanner as previously described and further including a CT scanner in which the inventive concepts disclosed herein can be implemented.

In an aspect, the invention may be used in conjunction with an integrated PET/CT imaging system. Referring to FIG. 6, a PET/CT imaging system 100 having the PET scanner 10 as previously described and further including a CT scanner 102 is shown. The CT scanner 102 includes a recording unit, comprising an x-ray source 104 and an x-ray detector 106. The recording unit rotates about the horizontal axis 25 during the recording of a tomographic image, and the x-ray source 104 emits x-rays 108 during a spiral recording. While an image is being recorded the patient 12 lies on the patient bed 15. The patient bed 15 is movably connected to a table base 110 such that it supports the patient bed 15 bearing the patient 15. The patient bed 15 includes a motor drive apparatus and is designed to continuously move the patient 12 along horizontal axis 25 through the tunnel 24 using continuous bed motion as previously described.

The table base 110 includes a control unit 112 connected to a computer 114 to exchange data. In the example shown in FIG. 6, a medical diagnostic or therapeutic unit is designed in the form of a system 100 by a determination unit 116 in the form of a stored computer program that can be executed on the computer 114. The computer 114 is connected to an output unit 118 and an input unit 120. The output unit 118 is, for example, one (or more) liquid crystal display (LCD) or plasma screen(s). An output 122 on the output unit 118 comprises, for example, a graphical user interface for actuating the individual units of the system 100 and the control unit 112. Furthermore, different views of the recorded data can be displayed on the output unit 118. The input unit 120 is for example a keyboard, mouse, touch screen or a microphone for speech input.

Figure 7:
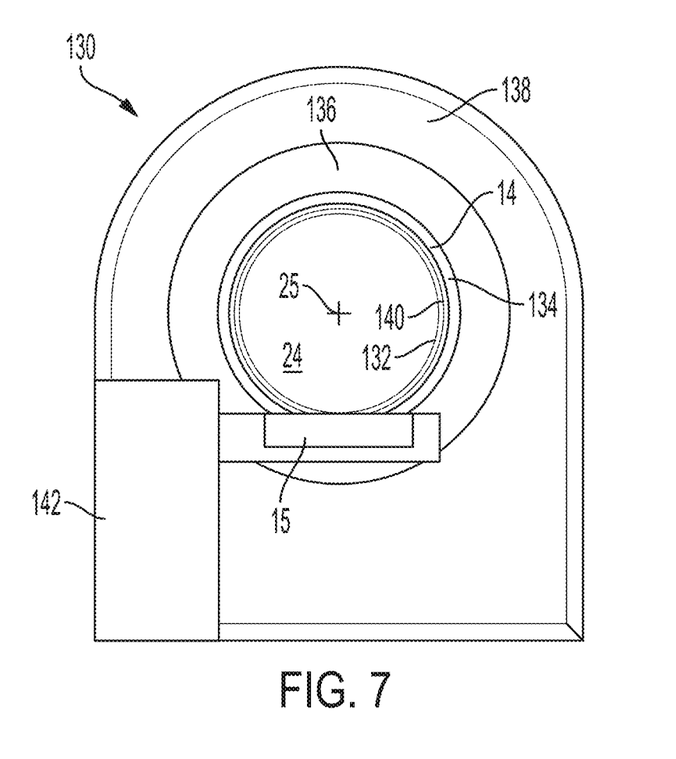
FIG. 7 depicts a front view of an integrated magnetic resonance (MR)/PET imaging system having the PET scanner as previously described and further including an MR scanner in which the inventive concepts disclosed herein can be implemented.

In an aspect, the invention may also be used in conjunction with an integrated MR/PET imaging system. The MR system may be used to generate an MR based attenuation map. Moreover, an MR based attenuation map may be compared to a PET based attenuation map and in the case of discrepancy the PET based map may be used to replace the MR based map in PET image reconstruction. Referring to FIG. 7, a front view of an MR/PET imaging system 130 is shown. The system 130 includes the patient tunnel 24 (see FIG. 1) that receives a patient to be scanned, an RF transmit antenna or body coil 132 (component of the MRI system), the PET gantry 14 that includes a gantry tube 134, a gradient coil 136 (a component of the MRI system) and superconducting magnet 138 (a component of the MRI system). The PET gantry 14 includes the PET detector rings 16 and an RF screen 140 (a component of the MRI system) located on the gantry tube 134. The system 130 further includes a table base 142 having a moveable patient bed 15 for moving a patient. The patient bed 15 is moveable in a horizontal direction 35 into and out of the patient tunnel 24 along the horizontal axis 25 of the system 130 to enable imaging of the patient by the system 130. The patient bed 15 includes a motor drive apparatus and is designed to continuously move the patient 12 along horizontal axis 25 through the tunnel 24 using continuous bed motion as previously described.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A method for generating transmission information in a time-of-flight positron emission tomography (PET) scanner having a patient tunnel and a plurality of PET detector rings wherein the PET scanner uses continuous bed motion to move a patient bed having a patient through the patient tunnel and wherein the patient receives a positron-emitting radioisotope dose prior to undergoing a PET scan, comprising:

storing the positron-emitting radioisotope in a radiation shielded container element;

moving the radioisotope into a stationary vessel located adjacent to the PET detector rings and within a field of view of the PET scanner at substantially the same time that the patient receives the radioisotope dose to form a stationary transmission source wherein the transmission information is generated while the patient bed undergoes the continuous bed motion; and withdrawing the radioisotope from the vessel when the PET scan is complete and storing the radioisotope in the container element wherein the PET scanner is integrated with an x-ray computed tomography (CT) scanner that generates a CT based attenuation map that is algorithmically compared to a PET based attenuation map wherein the PET based attenuation map is used to replace the CT based attenuation map in PET image reconstruction if a discrepancy occurs between the CT and PET based attenuation maps.

2. The method according to claim 1, further including:
(a) calculating a time-of-flight for emissions from the stationary transmission source for each pair of detectors in the PET scanner;
(b) defining a time window having a width centered around the calculated time-of-flight;
(c) measuring time-of-flight of actual emissions originating from the stationary transmission source without the patient in the field of view;
(d) comparing the measured time-of-flight from step (c) to the calculated time-of-flight and identifying the measured time-of-flight that are within the time window;
(e) identifying events from the stationary transmission source generated during step (c), thereby discriminating these events from emission events and random events to create a blank scan;
(f) measuring time-of-flight of actual emissions originating from the stationary transmission source with the patient in the field of view;
(g) comparing the measured time-of-flight from step (f) to the calculated time-of-flight and identifying the measured time-of-flight from step (f) that are within the time window;
(h) identifying events from the stationary transmission source generated during step (f), thereby discriminating these events from emission events and random events to create a transmission scan; and
(i) reconstructing the blank scan and the transmission scan to form the PET based attenuation map using an iterative reconstruction algorithm.

3. The method according to claim 1, wherein moving the radioisotope adjacent to the PET detector rings includes providing a tube element for receiving the radioisotope.

4. The method according to claim 3, wherein the tube element has a substantially spiral shape.

5. The method according to claim 1, wherein the radioisotope is an $^{18}$F radioisotope.

6. A stationary transmission source for a positron emission tomography (PET) scanner having a plurality of PET detector rings and a patient tunnel defined by a scanner cover wherein the PET scanner uses continuous bed motion to move a patient bed configured to support a patient through the patient tunnel and wherein the PET scanner is configured to provide a positron-emitting radioisotope dose to the patient prior to undergoing a PET scan, comprising:

a stationary tube element having a receiving end, wherein the tube is attached to a scanner surface of the scanner cover located adjacent to the PET detector rings and within a field of view of the PET scanner; and a pump device fluidly connected to the receiving end, wherein the pump device introduces the positron-emitting radioisotope into the tube and wherein the tube contains 7 ml of the radioisotope wherein transmission information is generated while the patient bed undergoes the continuous bed motion and wherein the radioisotope is withdrawn from the tube when the PET scan is complete.

7. The source according to claim 6, wherein the tube has a substantially spiral shape.

8. The source according to claim 7, wherein the spiral shape includes a plurality of spiral tube sections.

9. The source according to claim 8, wherein the spiral tube sections are separated by a sufficient distance to enable the spiral tube sections to extend in an axial range that covers the PET detector rings.

10. The source according to claim 6, wherein the pump device is a syringe.

11. The source according to claim 6, wherein the radioisotope is an $^{18}$F radioisotope.

12. A method for generating transmission information in a time-of-flight positron emission tomography (PET) scanner having a patient tunnel and a plurality of PET detector rings, wherein the PET scanner uses continuous bed motion to move a patient bed having a patient through the patient tunnel and wherein the patient receives a positron-emitting radioisotope dose prior to undergoing a PET scan, comprising:

storing the positron-emitting radioisotope in a radiation shielded container element;

provide a tube element for receiving the radioisotope wherein the tube element is stationary and is located adjacent to the PET detector rings and within a field of view of the PET scanner;

introducing the radioisotope into the tube element at substantially the same time that the patient receives the radioisotope dose to form a stationary transmission source wherein the transmission information is generated while the patient bed undergoes the continuous bed motion; and withdrawing the radioisotope from the tube element when the PET scan is complete and storing the radioisotope in the container element wherein the PET scanner is integrated with a magnetic resonance (MR) scanner that generates a MR based attenuation map that is algorithmically compared to a PET based attenuation map wherein the PET based attenuation map is used to replace the MR based attenuation map in PET image reconstruction if a discrepancy occurs between the MR and PET based attenuation maps.

13. The method according to claim 12, wherein the tube element has a substantially spiral shape.

14. The method according to claim 13, wherein the spiral shape includes a plurality of spiral tube sections.

15. The method according to claim 12, wherein the radioisotope is introduced into the tube element by a syringe.

16. The method according to claim 12, wherein the radioisotope is an $^{18}F$ radioisotope.

17. The method according to claim 12, wherein the tube element contains 7 ml of the radioisotope.

* * * * *